US005975401A

United States Patent [19]

Fealey

[11] Patent Number: 5,975,401

[45] Date of Patent: Nov. 2, 1999

[54] HAMMER-TYPE STAPLER WITH RELATIVELY MOVABLE DRIVER AND MAGAZINE

[75] Inventor: William S. Fealey, Jamestown, R.I.

[73] Assignee: Stanley Fastening Systems, LP, East Greenwich, R.I.

[21] Appl. No.: 09/083,501

[22] Filed: May 22, 1998

[51] Int. Cl.[6] .................................................... A61B 17/00

[52] U.S. Cl. .......................... 227/134; 227/133; 227/147

[58] Field of Search .................................... 227/133, 134, 227/147

[56] References Cited

U.S. PATENT DOCUMENTS

| | | | |
|---|---|---|---|
| 1,166,190 | 12/1915 | Dawson . | |
| 1,671,733 | 5/1928 | Maynard | 227/133 |
| 1,687,871 | 10/1928 | Maynard . | |
| 2,325,341 | 7/1943 | Polzer . | |
| 2,332,257 | 10/1943 | Polzer | 227/133 |
| 2,432,853 | 12/1947 | Barclay | 227/133 |
| 2,501,703 | 3/1950 | Wember | 227/133 |
| 2,537,601 | 1/1951 | Peterson | 227/133 |
| 2,645,773 | 7/1953 | Dugin | 227/133 |
| 2,653,317 | 9/1953 | Beckman . | |
| 2,661,999 | 12/1953 | Abrams . | |
| 2,664,565 | 1/1954 | Percoco . | |
| 2,667,639 | 2/1954 | Schick . | |
| 2,896,210 | 7/1959 | Rubin . | |
| 4,598,852 | 7/1986 | Olesen . | |

*Primary Examiner*—Peter Vo
*Assistant Examiner*—James P Calve
*Attorney, Agent, or Firm*—Pillsbury Madison & Sutro LLP

[57] ABSTRACT

A hammer-type stapler in which the staple driving element and the staple drive track defining structure are constructed and arranged with respect to the frame structure to move through a drive stroke incident to an operator grasping a handle portion and manually impacting the staple drive track defining structure on a workpiece to arrest the movement of the drive track structure on the workpiece while the frame structure and the staple driving element continue to move toward the workpiece with respect to the arrested drive track structure. The staple driving element is constructed and arranged with respect to the frame structure and the drive track structure such that the continued movement of the staple driving element toward the workpiece with respect to the arrested drive track structure is further and faster than the continued movement of the frame structure toward the workpiece with respect to the arrested drive track structure enabling the staple driving element to effect a drive stroke through the drive track and to drive a staple therein into the workpiece while the frame structure is undergoing a relative movement with respect to the drive track structure which is less than substantially equal to the relative movement of the staple driving element with respect to the drive track structure during the drive stroke of the staple driving element.

22 Claims, 5 Drawing Sheets

HAMMER-TYPE STAPLER WITH RELATIVELY MOVABLE DRIVER AND MAGAZINE

This application relates to staplers and more particularly to manually operated impact staplers sometimes referred to as hammer-type staplers.

BACKGROUND OF THE INVENTION

A typical hammer-type stapler includes a handle for enabling an operator to manually grasp the stapler and a frame which is fixed to or forms a part of the handle. The frame carries the usual staple driving components which include a structure defining a drive track, a staple driving element movable through the drive track and a magazine assembly for guiding a staple stick in the magazine assembly into the drive track so that successive leading staples are driven by the staple driving element through the drive track into the workpiece during the drive stroke of the staple driving element and for biasing a leading staple to move into the drive track during the return stroke of the staple driving element.

Staplers of the hammer-type which are known fall generally into two categories. Probably the most prevalent is the hammer-type stapler in which the staple driving element is fixed to the frame and handle. In this category, the magazine and staple drive track structure are moved with respect to the driver on impact. Examples of hammer-type staplers of the fixed driver- movable magazine category are exemplified in U.S. Pat. Nos. 2,664,565 and 2,667,639. In the other category, the magazine assembly and the drive track structure are fixed with respect to the frame and handle and the staple driving element is moved through the drive track in response to the impact. Examples of hammer-type staplers of this type are illustrated in U.S. Pat. Nos. 2,325,341 and 2,896,210.

Despite the fact that both fixed driver and fixed magazine hammer-type staplers have been known for decades, there always exists a need to improve the operation and efficiency of known devices.

BRIEF SUMMARY OF THE INVENTION

It is an object of the present invention to fulfill this continuing need with respect to hammer-type staplers. In accordance with the principles of the present invention, this objective is obtained by providing a hammer-type stapler comprising a frame structure including a hand grip portion constructed and arranged to be manually grasped by an operator. A magazine assembly includes structure defining a staple drive track which is mounted for relative movement with respect to the frame structure and structure defining a staple stick feed track leading to the staple drive track. A staple driving assembly is provided including a staple driving element mounted for relative movement with respect to the frame structure within the staple drive track through successive cycles each including a drive stroke and a return stroke. The magazine assembly includes a loading and feeding mechanism constructed and arranged to facilitate the manual loading of a staple stick into the feed track and to feed a loaded staple stick along the feed track in a feed direction so that successive leading staples are moved into the drive track to be driven therefrom in a dive direction into a workpiece during the drive stroke of successive cycles of the driving element. The driving element and the drive track structure are constructed and arranged with respect to the frame structure to move through a drive stroke incident to an operator grasping the hand grip portion and manually impacting the drive track structure on a workpiece to arrest the movement of the drive track structure on the workpiece while the frame structure and the staple driving element continue to move toward the workpiece with respect to the arrested drive track structure. The staple driving element is constructed and arranged with respect to the frame structure and the drive track structure such that the continued movement of the staple driving element toward the workpiece with respect to the arrested drive track structure is further and faster than the continued movement of the frame structure toward the workpiece with respect to the arrested drive track structure enabling the staple driving element to effect a drive stroke through the drive track and to drive a staple therein into the workpiece while the frame structure is undergoing a relative movement with respect to the drive track structure which is less than substantially equal to the relative movement of the staple driving element with respect to the drive track structure during the drive stroke of the staple driving element. A spring system is provided which is constructed and arranged to effect opposite relative movements between the driving element and drive track structure with respect to the frame structure during which the staple driving element is moved within the drive track through a return stroke.

In accordance with the principles enunciated above, an improvement in operating characteristics and efficiency is achieved by essentially moving two structures with respect to the frame structure approximately one half the distance of the stroke itself rather than one structure through the entire stroke while the other structure is held stationary in its broadest aspects, the present invention contemplates that the relative motion of the staple-driving element can be accomplished by a movable workpiece striking element separate from the magazine such as disclosed in the '210 patent previously cited. However, it is greatly preferred that this relative motion be accomplished by the magazine itself since, in accordance with the principles of the present invention, the magazine has a relative movement as well.

The principles of the present invention have applicability to hammer-type staplers in which the feed track is related to the drive track in conventional perpendicular fashion. However, the hammer-type stapler disclosed herein has an overly canted drive track. This feature, which is claimed in my concurrently filed application, is provided to alleviate the knuckle-busting problem and is preferred in combination with the features of the present invention already mentioned.

DETAILED DESCRIPTION OF THE PREFERRED EMBODIMENT OF THE INVENTION

Figure 1:
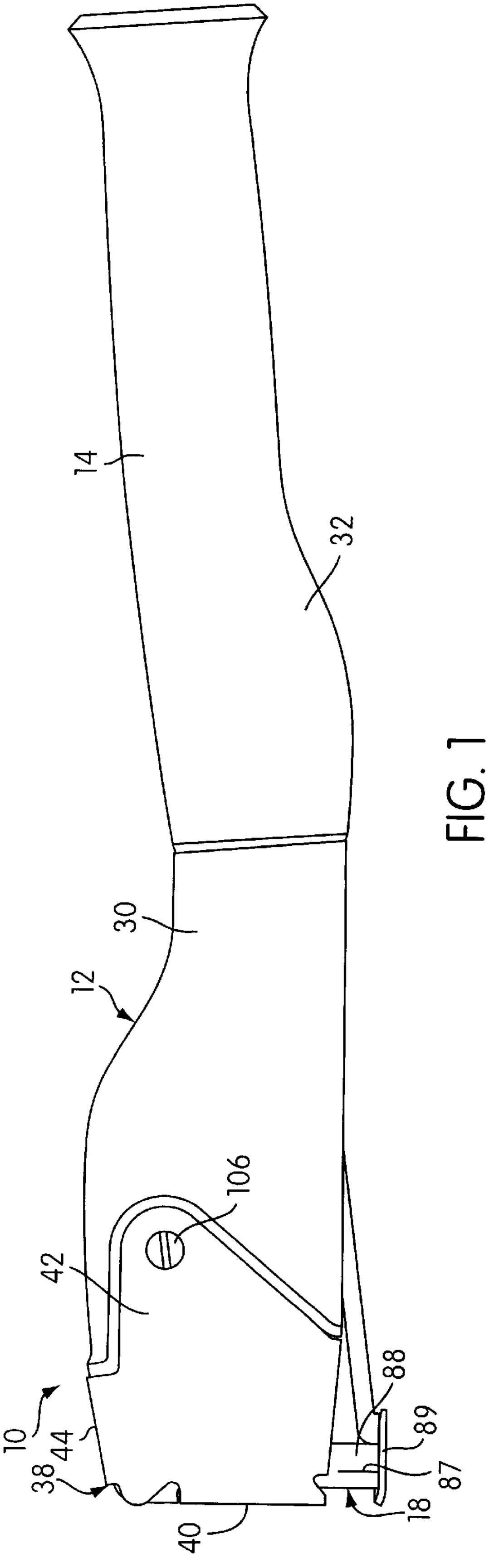
FIG. 1 is a side elevational view of a hammer-type stapler embodying the principles of the present invention.
Figure 2:
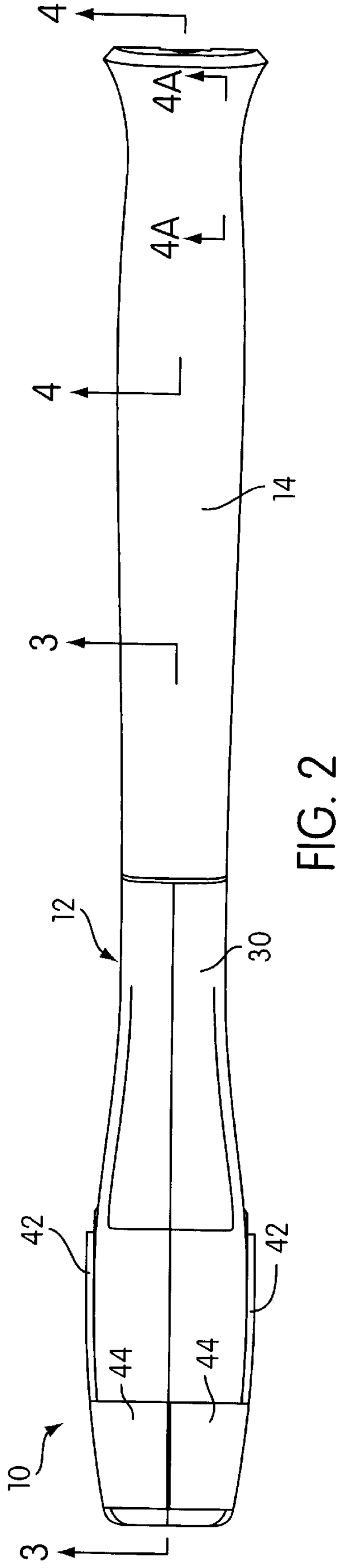
FIG. 2 is a top plan view thereof.

Referring now more particularly to the drawings, there is shown in FIGS. 1 and 2 thereof a stapler of the hammer-type, generally indicated at 10, which embodies the principles of the present invention. In general, the stapler 10 includes an elongated fore and aft extending frame structure, generally indicated at 12, which includes a handle or hand grip portion, generally indicated at 14, at its rearward end portion, the frame structure extending forwardly of the hand grip portion 14. Mounted within the frame structure 12 for relative movement with respect thereto is a magazine assembly, generally indicated at 16, which includes structure defining a staple drive track, generally indicated at 18, and structure defining a staple stick feed track, generally indicated at 20, which leads to the drive track 18. Also mounted on the frame structure 12 for relative movement with respect thereto is a staple driving assembly, generally indicated at 22, which includes a staple driving element 24 mounted within the drive track 18.

The magazine assembly 16 also includes a loading and feeding mechanism, generally indicated at 26, which is constructed and arranged to facilitate the manual loading of a staple stick into the drive track and to guide a loaded staple stick along the feed track 20 so that a leading staple is biased to move into the drive track 18.

The driving element 24 and the drive track structure 18 are constructed and arranged with respect to the frame structure 12 to move through a drive stroke incident to an operator grasping the hand grip portion 14 and manually impacting the drive track structure 18 on a workpiece during which drive stroke the total distance of relative movement between the driving element 24 and drive track structure 18 is accomplished by a movement of the driving element 24 with respect to the frame structure 12 a distance less than the total distance and a movement of the drive track structure 18 with respect to the frame structure 12 a distance less than the total distance which, when added to the distance of movement of the driving element 24, is equal to the total distance. A spring system, generally indicated at 28, is provided which is constructed and arranged to effect a relative movement between the driving element 24 and the drive track structure 18 which respect to the frame structure 12 through a return stroke during which the total distance of relative movement between the driving element 24 and the drive track structure 18 is accomplished by movement of the driving element 24 with respect to the frame structure 12 a distance less than the total distance and a movement of the drive track structure 18 with respect to the frame structure 12 a distance less than the total distance which when added to the distance of movement of the driving element 24 is equal to the total distance. The drive track structure 18 and the feed track structure 20 are constructed and arranged so that the direction of guided movement of the staple stick along the feed track 20 is at an angle greater than 90° with respect to the direction of the drive stroke of the driving element 24 within the drive track 18 so that the staple crown enters the drive track 18 while the lower penetrating ends of the staple legs are displaced angularly with respect to the direction of the drive stroke. The drive track structure 18 is constructed and arranged to cause the leading staple to be moved into alignment with the drive track 18 during the drive stroke movement so as to be driven into the workpiece in the direction of the drive stroke enabling the hand grip portion 14 to be positioned for manual gripping so that the knuckles are spaced from a flat workpiece surface in which a staple has been driven generally perpendicularly therein.

Figure 3:
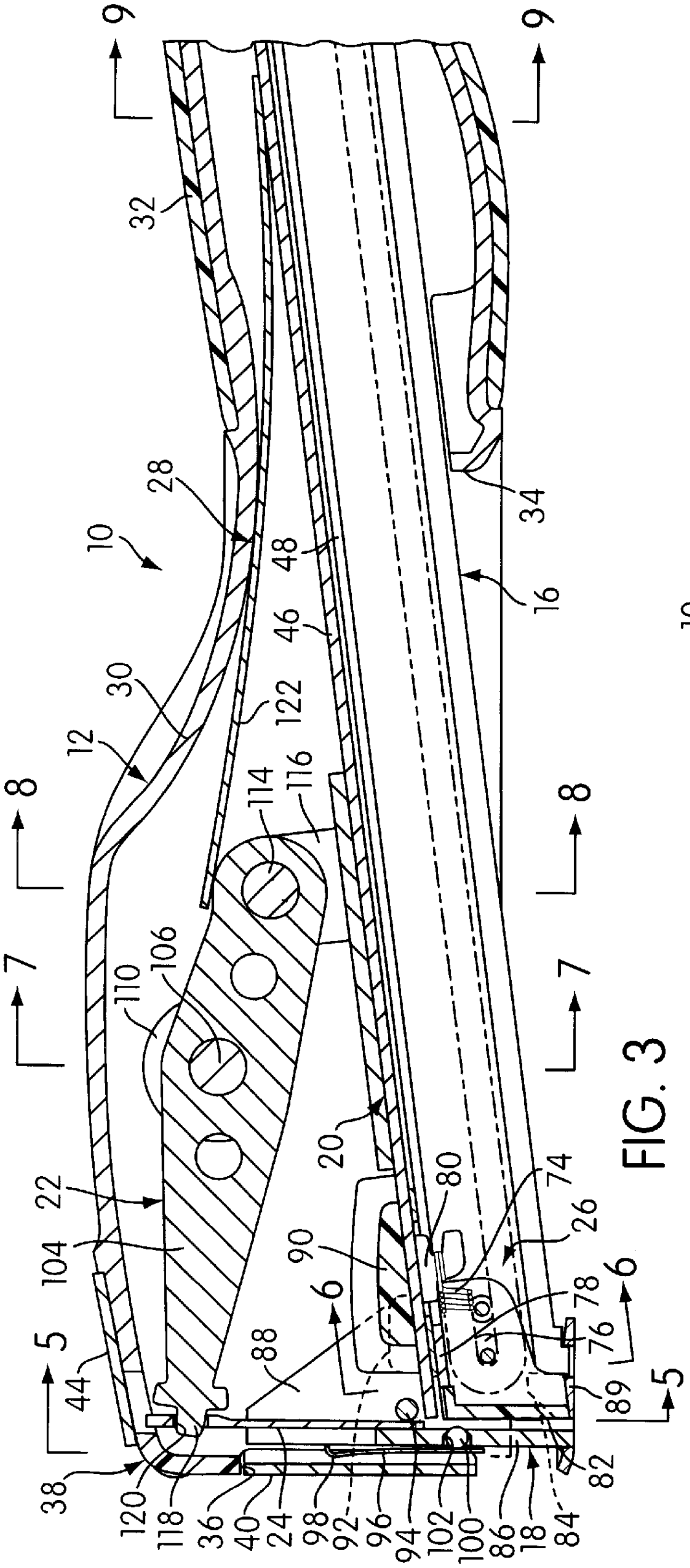
FIG. 3 is an enlarged fragmentary sectional view taken along the line 3—3 of FIG. 2.
Figure 4:
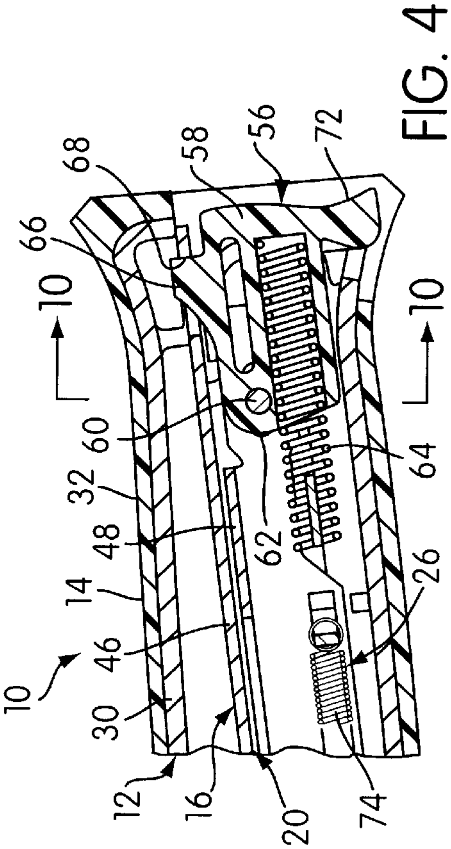
FIG. 4 is an enlarged fragmentary sectional view taken along the line 4—4 of FIG. 2.

Referring now more particularly to FIGS. 3 and 4, it can be seen that the frame structure 12 is hollow and elongated in the front-to-rear direction. The hollow frame structure 12 is in the form of a frame member 30 which is constructed from two halves fixedly interconnected together, as by a series of fasteners or the like. The rear portion of the frame member 30, together with a resilient sleeve 32 which is mounted thereover, defines the hand grip portion 14 of the frame structure 12. The frame member 30 extends forwardly of the hand grip portion 14. As best shown in FIG. 3, this forwardly extending portion is open along a lower extent thereof, as indicated at 34, and along a lower forward extent thereof, as indicated at 36.

The frame structure 12 also includes a front exterior cover member, generally indicated at 38, which comprises a forward wall 40 disposed in closing relation to the forward opening 36 of the frame member 30 and a pair of rearwardly bent side walls 42 overlapping forward side portions of the frame member 30. Formed integrally at the upper forward edges of the cover side walls 42 are two short top walls 44 which are bent inwardly toward one another to overlie the upper forward portion of the frame member 30. The top walls 44 are available to function as a hammering surface for staples which have been driven improperly and must be made flush with the workpiece surface.

The feed track structure 20 of the magazine assembly 16 is preferably constructed and arranged to accommodate two staple sticks. The feed track structure 20 includes an elongated housing member 46 of inverted U-shaped cross-sectional configuration disposed in exterior confining relation to staples loaded in the magazine assembly 16 and an elongated core member 48 mounted for movement between (1) an operating position disposed in interior confining relation to staples loaded in the magazine assembly 16 and (2) a loading position disposed in a position to provide access for the insertion of a staple stick into the housing member 46 through the U-shaped cross-sectional configuration thereof. In the preferred embodiment shown, the core member 48 is also of inverted U-shaped cross-sectional configuration and is longitudinally slidably mounted within the housing member 46 so as to extend through and rearwardly of the hollow handle portion when in the loading position thereof.

Figure 4A:
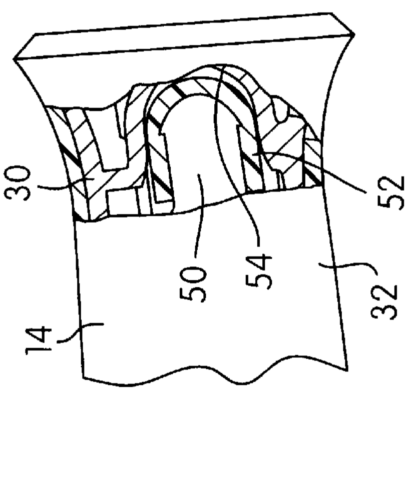
FIG. 4A is an enlarged fragmentary sectional view taken along the line 4A—4A of FIG. 2.

The housing member 46 is movably mounted within the frame member 30 so that the forward end swings with respect to the frame member 30 from a normal inoperative position, as shown in FIGS. 1 and 3, into an upwardly displaced operative position in response to the impacting of the drive track structure 18 with a workpiece. The extent of the movement is approximately one-half the distance of the drive stroke of the staple driving element 24 with respect to the drive track structure 18. The manner in which the housing member 46 is mounted within the frame member 30 is best shown in FIG. 4A. The depending legs of the U-shaped cross-section of the housing member includes two laterally spaced rearwardly extending extensions 50 having small spaced barbs extending from the upper and lower edges thereof. Extended over each extension 50 is a flat bearing sleeve 52 which is retained, in position by the barbs. The bearing sleeves 52 fit within laterally spaced receiving surfaces 54 formed in the rearward end of the frame member 30 shaped to allow the bearing sleeves to pivot about a transverse axis in conjunction with a limited amount of longitudinal movement.

The mounting of the core member 48 with respect to the housing member 46 forms a part of the loading and feeding mechanism 26 of the magazine assembly 16. In order to retain the core member 48 in its operating position so that it can be selectively moved into its loading position, there is provided a releasable latch assembly, generally indicated at 56. The latch assembly 56 basically functions to releasably retain the core member 48 in the operating position thereof. Preferably, it also is constructed and arranged to allow the core member 48 when in its operating position to resiliently yieldingly move rearwardly in response to a staple jam occurrence during a drive stroke.

Figure 10:
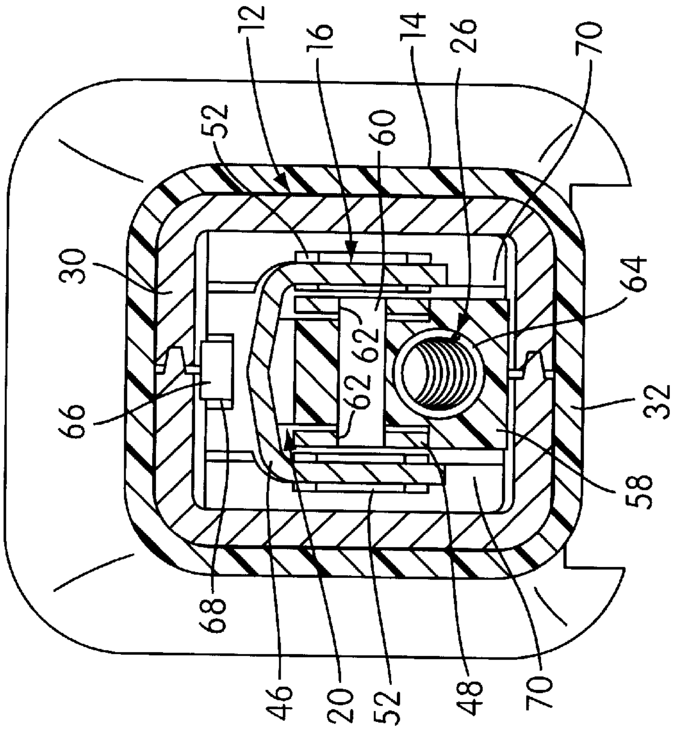
FIG. 10 is a sectional view taken along the line 10—10 of FIG. 4.

To this end, as best shown in FIGS. 4 and 10, the latch assembly 56 includes a latch member 58 having a pivot pin 60 extending laterally through the forward portion thereof. The opposite ends of the pivot pin 60 extend outwardly of the latch member 58 and into horizontal slots 62 formed in the legs of the U-shaped core member 48. The latch member 58 includes a forwardly opening bore below the pivot pin 60 which receives the rear end portion of a compression coil spring 64, the forward end of which bears against tab structure struck and bent from the core member 48. The spring 64 thus serves to resiliently bias the core member 48 forwardly into its operating position and the latch member 58 rearwardly. The rearward spring bias of the latch member 58 is resisted by the engagement of an upwardly and rearwardly disposed latch member catch 66 against an edge 68 defining an opening in the top wall of the housing member 46 and by the engagement of lateral stop portions 70 (see FIG. 10) of the latch member 58 upwardly against the downwardly facing free edges of the legs of the core member 48. The latch member 58 includes a rear digital engaging portion 72 which can be digitally engaged and moved downwardly to release the latch member 58 by a clockwise pivotal action, as viewed in FIG. 4, to allow the core member 48 to be moved rearwardly from its operating position to its loading position.

At a position just forwardly of the end of spring 64, an additional tab structure is struck and bent from the core member 48 to secure the lower rear end of a tension coil spring 74. The coil spring 74 extends forwardly and is trained about a grooved roller 76 rotatably carried by a core tip 78 fixed to the forward end of the core member 48. The coil spring 74 extends rearwardly from the roller 76 and has its opposite end fixed to a pusher 80 riding within a central longitudinal slot in the top wall of the core member 48 and within the staple space defined by the housing member 46 and core member 48. The spring 74, roller 76 and pusher 80 form a part of the loading and feeding mechanism 26 of the magazine assembly 16.

The core tip 78 forms a part of the drive track structure 18. Specifically, the core tip 78 includes a forwardly facing planar surface 82 which defines the lower central rearward portion of the drive track 18. The upper edge of the surface 82 constitutes a cut-off edge for the magazine beyond which the crown of the leading fastener extends when moved into the drive track. The edge and the upper surface of the core tip 78 extending rearwardly thereof support the staple next to the leading staple to facilitate cutoff from the staple stick during the drive stroke.

In accordance with the principles of the present invention, the surface 82, as well as the drive track 18 itself, rather than being at right angles to the feed track 20 is at a slightly greater angle, as, for example, approximately 97°, so that when the crown of the leading staple moves from the feed track to the drive track, the penetrating free ends of the staple legs are displaced rearwardly from the surface 82. Extending laterally outwardly from opposite sides of the lower end of the surface 82 are integral portions which define two spaced forwardly and downwardly slanted cam surfaces 84 leading to the surface 82 at their lower end. The cam surfaces 84 extend downwardly in flush relation with the surface 82 to form spaced forwardly facing stop surfaces 85. The lower ends of the legs of the inverted U-shaped housing member 46 are offset laterally outwardly in order to slidably accommodate the integral core tip portions which define the cam surfaces 84. The cam surfaces 84 are in a position to be engaged by the free ends of the legs of a staple being driven in the event that it has not been aligned with the canted drive track 18 as it reaches the level of the surfaces 84.

The drive track structure 18 also includes a track member which includes a front wall 86, having parallel side walls 88 extending rearwardly therefrom. The portion of the side walls 88 which are coextensive with the housing member 46 are fixed, as by welding or the like, to the housing member 46. Fixed to the lower end of the track member and housing member 46 is a plate 89 which provides a workpiece striking surface for the fixedly interconnected drive track structure 18 and feed track structure 20.

Figure 5:
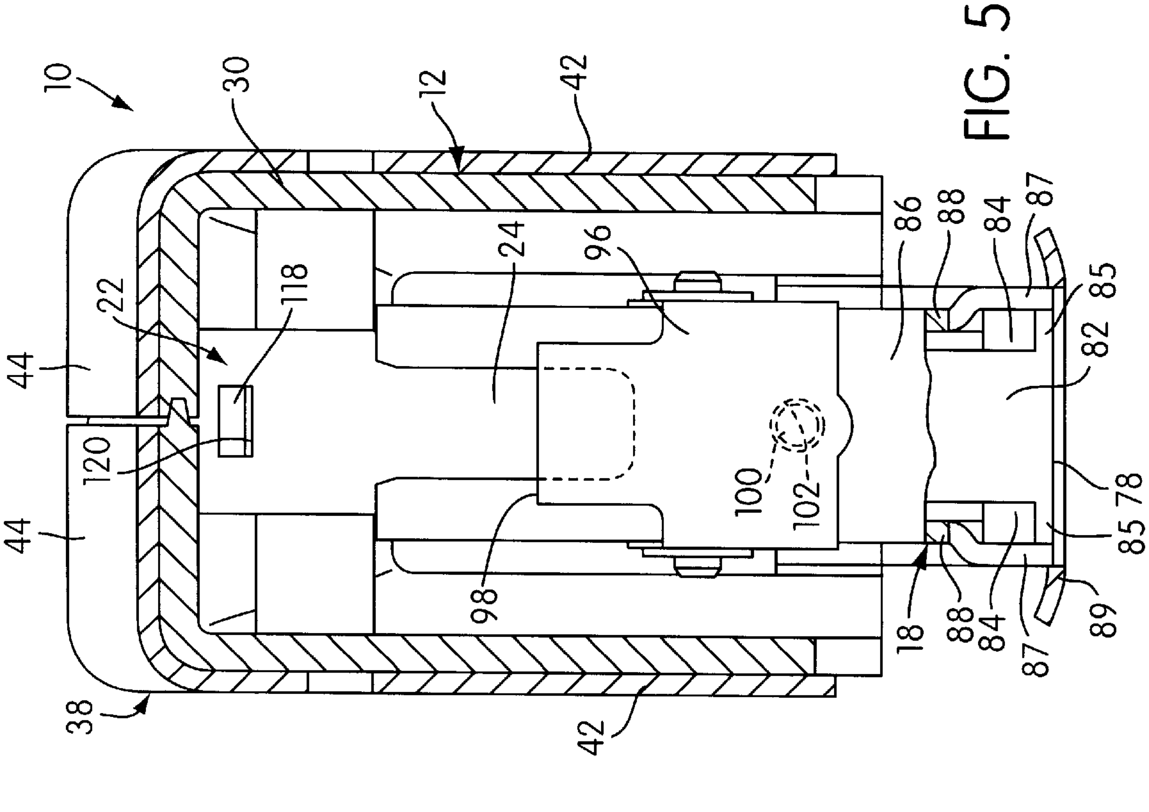
FIG. 5 is a sectional view taken along the line 5—5 of FIG. 3.

As best shown in FIG. 5, the lower rearward portion of the side walls 88 are lanced laterally outwardly along a cut 87. The rearwardly facing edge of which provide surfaces which are engaged by the stop surfaces 85 of the core tip 78 under the bias of spring 64.

Figure 6:
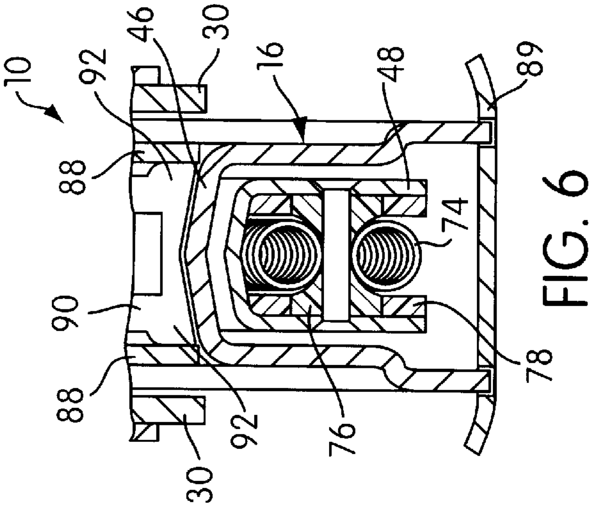
FIG. 6 is a sectional view taken along the line 6—6 of FIG. 3.

As best shown in FIGS. 3, 5 and 6, a shock absorbing pad 90 is mounted on the top wall of the housing member 46. The pad 90 includes a pair of laterally outwardly extending flange portions 92 which are engaged by the lower edges of the side walls 88 to retain the pad 90 in position. Extending between the side walls 88 forwardly of the pad 90 is a pin 94 the forward surface of which defines the rear surface of the drive track above the housing member 46.

The opposite ends of the pin 94 extend outwardly of the side walls 88 and pivotally receive the legs of a U-shaped spring member 96. The spring member 96 includes a front in-turned upper portion 98 which serves to bias the spring member 96 to pivot about the pin 94. The lower rear surface of the U-shaped spring member engages a ball 100 disposed within an opening 102 formed in the front track member wall 86. The opening 102 is shaped to allow the ball 100 to protrude rearwardly into the drive track at a position which is centrally located just below the crown of a leading staple fed from the feed track into the drive track. The ball 100 is engaged by the staple crown just after the staple is stripped from its stick and this engagement facilitates alignment of the angular engagement of the end of the staple driving element 24 with the upper surface of the staple crown which aligns the staple legs with the overly angled drive track.

Figure 7:
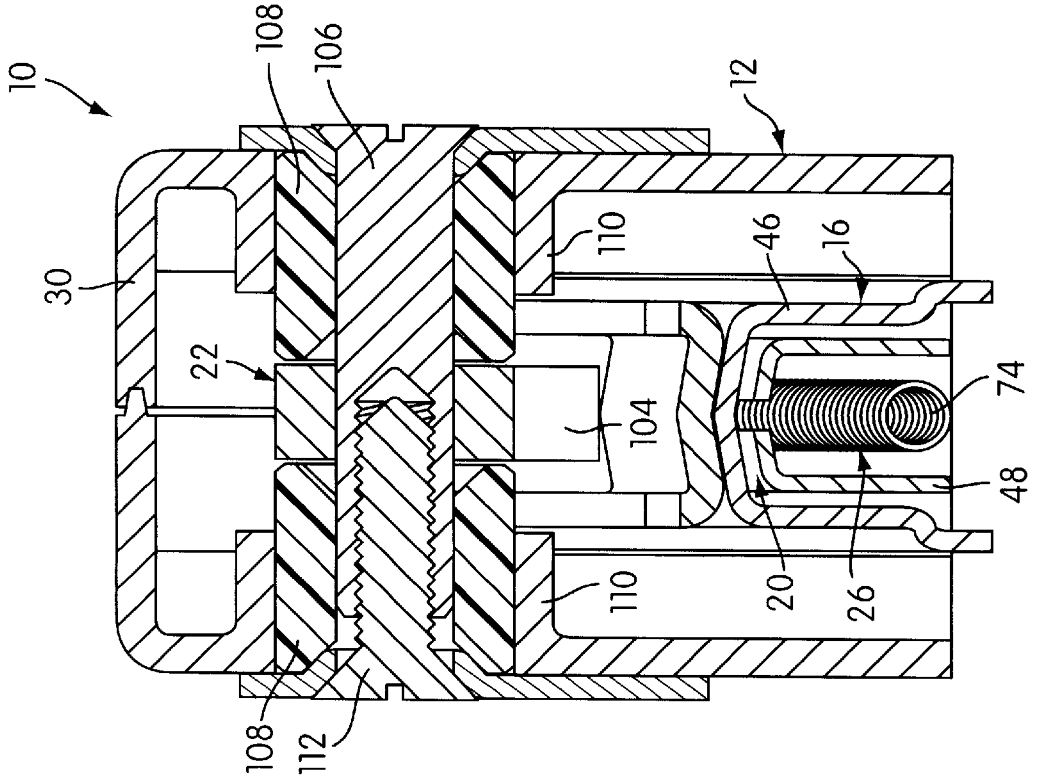
FIG. 7 is a sectional view taken along the line 7—7 of FIG. 3.

The staple driving assembly 22 includes a motion-transmitting mechanism in the form of a lever 104 pivoted to the frame member 30 and interconnected between the housing member 46 and the staple driving element 24. As best shown in FIGS. 3 and 7, the lever 104 is pivoted intermediate its ends by a pivot pin 106 in the form of a flat-headed bolt with an internally threaded bore in its shank. The pivot pin 106 extends within a pair of resilient bushings 108 disposed on opposite sides of the lever 104. Bushings 108 are seated within in-turned opposed opening-defining annular flanges 110 formed in the frame member 30. The side walls 42 of the cover member are also apertured and countersunk to allow the pin 106 to extend therethrough in a position to receive the flat head in one side wall 42. A smaller flat head bolt 112 is threaded within the threaded shank bore of the pin 106 to complete the pivotal mounting of the lever which by virtue of the resiliency of the bushings 108 is allowed to have a limited amount of transverse movement. Bushings 108 are preferably formed of a suitable rubber but they may be plastic or other elastomeric material.

Figure 8:
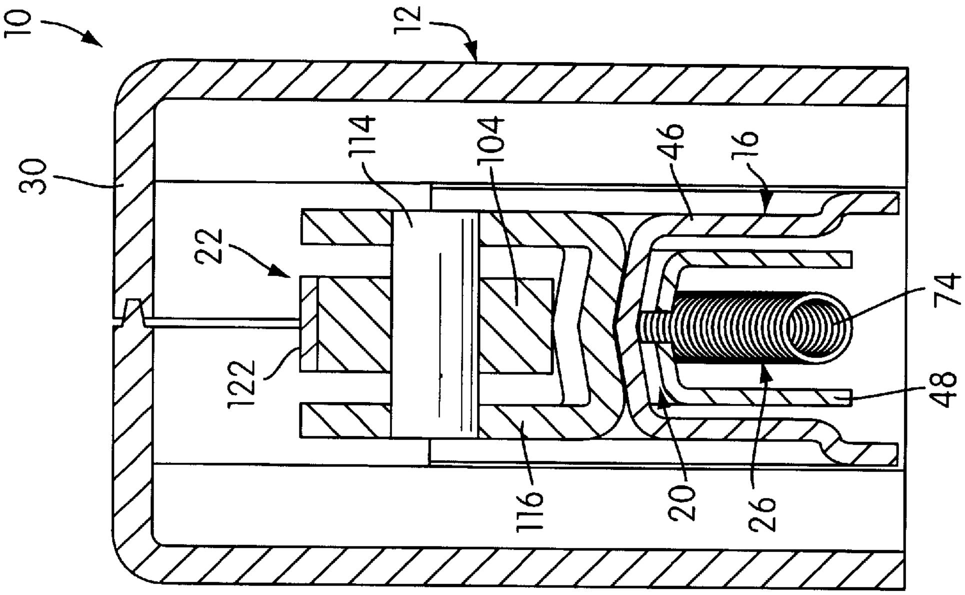
FIG. 8 is a sectional view taken along the line 8—8 of FIG. 3.

As best shown in FIG. 3 and 8, the rearward end of the lever 104 is pivotally connected with the housing member 46 by a pivot pin 114 which extends through the lever 104 and has its ends fixed to the legs of a U-shaped bracket 116 fixed to the upper wall of the housing member 46. The forward end of the lever 104 includes a protusion 118 which extends within an opening 120 formed in the upper end of the staple driving element 24.

Figure 9:
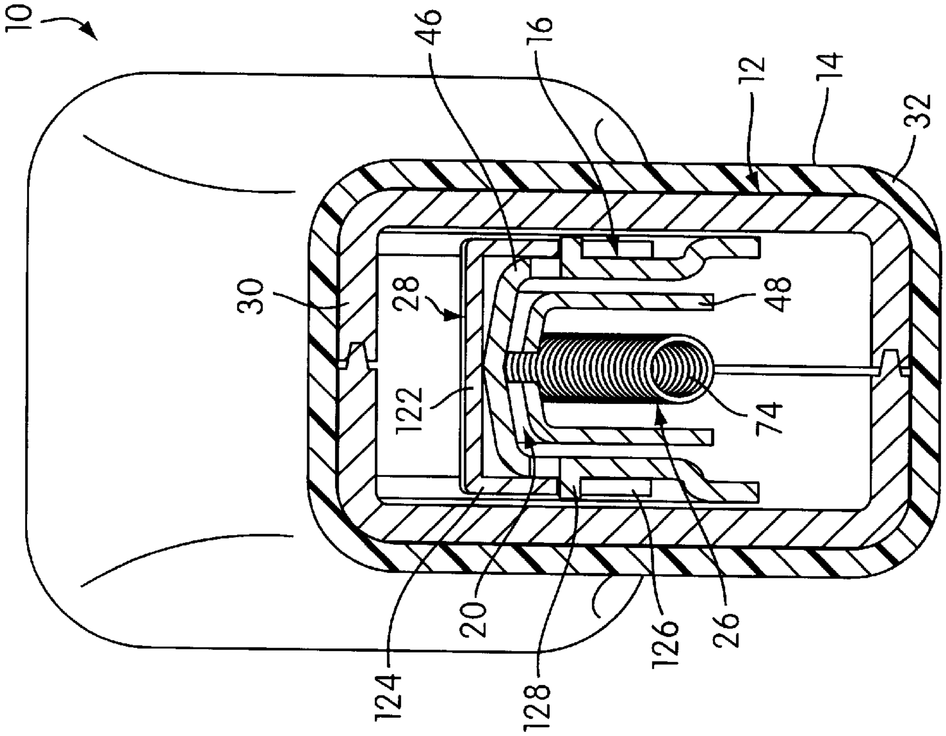
FIG. 9 is a sectional view taken along the line 9—9 of FIG. 3.

As best shown in FIGS. 3 and 9, the spring system 28 is in the form of a flat leaf spring 122 having a front end engaged with the rear end of the lever 104. A mid-portion of the flat leaf spring 122 is disposed in flexed engagement with an interior downwardly facing surface of the frame member 30 just forwardly of the forward end of the hand grip portion 14. The rear of the flat leaf spring includes two integral downwardly turned ears 124 spaced apart so as to embrace the legs of the U-shaped housing member 46. The ears 124 have downwardly opening recesses 126 therein to receive two tabs 128 cut and bent outwardly from the legs of the housing member 46 to retain the spring 122 in operating position.

Operation

In the operation of the hammer-type stapler 10, the operator simply grips the hand portion 14 and swings the stapler 10 in a hammer-like movement into the workpiece where the staple is to be driven. When the plate 89 strikes the workpiece, the staple drive track structure 18 and feed track structure 20 will have its movement arrested while the frame member 30 continues to move in a direction toward the workpiece. This relative movement of the housing member 46 with respect to the frame member 30 causes the pivot pin 114 to move upwardly which, in turn, effects a downward movement of the forward end of the lever 104 which carries with it the staple driving element 24. In this way, the staple driving element 24 is simultaneously moved with respect to the housing member 30 with the staple drive track structure 18 and feed track structure 20. During the drive stroke of the staple driving element 24 within the drive track, the lower end thereof will initially engage the crown of the leading staple fed from the feed track into the drive track. Since the upper surface of the crown is at an angle with respect to the lower surface of the staple driving element 24, the interengagement therebetween will tend to both strip the leading fastener from the stick within the feed track and to move the lower end of the legs forwardly toward alignment with the drive track. Immediately after the staple is stripped, the forward lower surface of the staple crown will engage the ball 100 and this engagement, in turn, will tend to align the legs of the staple with the drive track. As the staple is moved past the ball 100, the ball 100 moves within the opening 102 against the bias of the spring member 96 where it is retained by the presence of the staple driving element 24 during the remainder of the drive stroke and the subsequent portion of the return stroke until the end moves above the ball 100.

In the event that the legs of the staple have not been aligned with the drive track, the free ends of the legs will engage the cam surfaces 84 and, as the driving movement of the staple continues, the staple will be fully aligned with the drive track so as to enter the workpiece in a perpendicular relationship. In this regard, it will be noted that the hand grip portion 14 is spaced from a flat workpiece which has been engaged by the plate 89 and had a staple driven perpendicularly therein. This relationship practically eliminates the problem of the operator's knuckles striking the workpiece in normal operation on floors and roofs.

During the drive stroke, the leaf spring 122 is stressed by virtue of the upward movement of the rear end of the lever 104 so that as soon as the drive stroke is completed, the spring 122 will serve to return the staple drive track structure 18 and feed track structure 20 as well as the staple driving element 24 back into the inoperative positions thereof, as shown in FIG. 3. The staples disposed within the feed track are resiliently urged in a forward direction to move the leading staple of the stick into the drive track by virtue of the pusher 80 biased by the spring 74. As soon as the lower end of the staple driving element 24 passes the crown of the leading staple in the feed track during the return stroke, the leading staple will then be biased into the drive track to complete the cycle and condition the stapler for another driving action.

If during a drive stroke, a staple should become jammed, the core member 48 and the surface 82 of the core tip 78 which is fixed thereto can move rearwardly by virtue of the interconnection of the core member 48 with the latch assembly 56. Specifically, the core member 48 is capable of being moved resiliently rearwardly against the action of spring 64 since the latch member 58 is retained in the position shown in FIG. 4 against rearward movement by virtue of the engagement of the catch 66 with the surface 68 and the flanges 70 with the undersides of the legs of the core member 48 as shown in FIG. 10. Since the core member 48 can move rearwardly by virtue of the elongated slot 62 which receives the pin 60 and is biased forwardly by the spring 64, a yielding rearward movement of the core tip 78 and core member 48 can take place in the event of a staple jam.

When all of the staples within the feed track have been driven into the workpiece and it is desired to continue, the latch member 58 is digitally engaged at the rear portion 72 so as to pivot the latch member 58 from the core member retaining position shown in FIG. 4 in a clockwise direction into a core member releasing position, wherein the catch 66 extends below the opening 68, thus allowing the entire core to slide rearwardly and exposing the interior of the housing member 46 through the opening 34. The supply of staples can be replenished by simply dropping a staple stick into the housing member 46 in an inverted relation with the crowns of the stick downwardly. While the opening is not big enough to receive two sticks, the arrangement is such that a first stick can be moved into the housing member 46 and then moved rearwardly in order to provide space for the insertion of a second stick. After two staple sticks have been loaded within the housing member 46, the core member 48 is moved forwardly and during the end of this movement, which is determined by the engagement of forwardly facing stop surfaces 85 with the rearwardly facing edges of cuts 87, the latch member 56 will be cammed by the forward surface of the catch 66 from its core retaining position into its core releasing position and then returned by the action of the spring 64 into its core retaining position to enable the stapler to again be used to drive staples.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A hammer-type stapler comprising a frame structure including a hand grip portion constructed and arranged to be manually grasped by an operator, a magazine assembly including structure defining a staple feed track and a staple drive track disposed at a distal end thereof, said staple feed track and said drive track being mounted for relative movement with respect to said frame structure a staple driving assembly including a staple driving element mounted for relative movement with respect to said frame structure within said drive track through successive cycles each including a drive stroke and a return stroke, said magazine assembly including a loading and feeding mechanism constructed and arranged to facilitate the manual loading of a staple stick into said feed track and to feed a loaded staple stick along said feed track in a feed direction so that successive leading staples are moved into said drive track to be driven therefrom in a drive direction into a workpiece during the drive stroke of successive cycles of said driving element, said driving element and said drive track structure being constructed and arranged with respect to said frame structure to move through a drive stroke incident to an operator grasping said hand grip portion and manually impacting the drive track structure on a workpiece to arrest the movement of the drive track structure on the workpiece thereby arresting downward movement of said staple feed track structure while said frame structure and said staple driving element continue to move toward said workpiece with respect to the arrested drive track structure;

motion transmitting structure being constructed and arranged with respect to said driving element, said frame structure and said drive track structure such that the continued movement of said driving element toward said workpiece with respect to the arrested drive track structure is further and faster than the continued movement of the frame structure toward said workpiece with respect to the arrested drive track structure enabling said driving element to effect a drive stroke through said drive track and to drive a staple therein into said workpiece while said frame structure is undergoing a relative movement with respect to said drive track structure which is less than substantially equal to the relative movement of said driving element with respect to said drive track structure during the drive stroke of said driving element, and a spring system constructed and arranged to effect opposite relative movements between said driving element and drive track structure with respect to said frame structure during which said driving element is moved within said drive track through a return stroke.

2. A hammer-type stapler as defined in claim 1 wherein said hand grip portion forms a rearward portion of said frame structure which extends forwardly therefrom, said feed track structure including an elongated housing member extending within said frame structure in a direction front to rear with a rearward end portion thereof movably supported on a rearward portion of said frame structure, said drive track structure being fixed to a forward end portion of said housing member so that when an operator grasps the handle portion and impacts the drive track structure on a workpiece the frame structure continues to move with a pivotal action with respect to the housing member, wherein said motion transmitting structure includes a motion transmitting mechanism for transmitting the relative movement between said frame structure and said housing member to a relative movement of said driving element with respect to said frame structure so that the relative movements of both the driving element and the drive track structure with respect to said frame structure during the impacting operation results in a relative drive stroke movement of said driving element within said drive track.

3. A hammer-type stapler as defined in claim 2 wherein said motion-transmitting mechanism includes a lever having an intermediate portion thereof mounted on a forward portion of said frame structure above said housing member for pivotal movement about a transverse axis with respect to said frame structure, said lever having a rearward end portion connected to move with said housing member and a forward end portion connected to move with said driving element.

4. A hammer-type stapler as defined in claim 3 wherein the intermediate portion of said lever is pivotally mounted on said frame structure by a resilient bushing which allows said lever to have a limited amount of resiliently yielding movement in a direction transverse to the pivotal axis thereof.

5. A hammer-type stapler as defined in claim 4 wherein the connection between the rearward end portion of said lever and housing member is a pivotal connection about an axis parallel with the pivotal axes of said lever and said housing member.

6. A hammer-type stapler as defined in claim 4 wherein the connection between the forward end of said lever and said driving element is a sliding engagement of a forward end portion of said lever within an opening in an end of said driving element opposite from an end thereof which engages a staple during the drive stroke thereof.

7. A hammer-type stapler as defined in claim 6 wherein said housing member is movably mounted on said frame structure by a pair of transversely spaced rearwardly extending semi-circular bearing sleeves slidably and pivotally received in suitably contoured surfaces at the rearward portion of said frame structure.

8. A hammer-type stapler as defined in claim 7 wherein said spring system includes a leaf spring having a rear end portion connected with said housing member, an intermediate portion engaging said frame structure and a forward end engaging the rear end of said lever to bias the same in a direction to cause said driving element to be moved through said return stroke.

9. A hammer-type stapler as defined in claim 8 wherein said drive track structure and said staple feed track structure are constructed and arranged so that the direction of guided movement of a staple stick along said feed track is at an angle greater than 90° with respect to the direction of the drive stroke of said driving element within said drive track so that a staple crown of a leading staple enters the drive track while a pair of staple legs of the leading staple is displaced angularly with respect to the direction of the drive stroke, and wherein said drive track structure is constructed and arranged to cause the leading staple to be moved into alignment with the drive track during the driving movement imparted to the crown thereof during said drive stroke enabling the hand grip portion to be positioned for manual gripping so that knuckles of a hand gripping said hand grip portion are spaced from a flat workpiece surface in which a staple has been driven generally perpendicularly therein.

10. A hammer-type stapler as defined in claim 9 wherein said staple drive track defining structure includes a staple-aligning assembly constructed and arranged to be yieldingly engaged beneath a forward crown portion of a leading staple disposed in said drive track slightly after said leading staple has been stripped from the staple stick during the drive stroke thereof to cause a pair of legs of the staple to move into alignment with the crown of the staple within said drive track.

11. A hammer-type stapler as defined in claim 10 wherein said staple-aligning assembly includes a ball mounted for fore and aft movement in said drive track structure in a position slightly below a crown of a leading staple moved into said drive track by said magazine loading and feeding mechanism, and a spring constructed and arranged to bias said ball so that a rearward portion thereof enters said drive track to be engaged and moved forwardly against the bias of said spring as the crown of the staple is moved thereby during the drive stroke thereof.

12. A hammer-type stapler as defined in claim 11 wherein said staple drive track defining structure includes a staple-camming structure disposed rearwardly of said drive track constructed and arranged to engage a pair of free ends of a pair of legs of a staple being driven in misalignment with said drive track and to cam the free ends of the legs of the staple into alignment with said drive track before moving outwardly thereof into the workpiece during the drive stroke thereof.

13. A hammer-type stapler as defined in claim 1 wherein said feed track structure includes an elongated exterior housing member for containing therein a plurality of staple sticks containing staple crowns and staple legs in exterior confining relation to the staple crowns and the staple legs, and a core member movable with respect to said housing member between (1) an operating position disposed in interior confining relation to the staple crowns and staple legs and (2) a loading position withdrawn from said operative position so as to enable a staple stick to be loaded into said exterior housing member in a direction toward a portion thereof confining the staple stick above the staple crowns thereof.

14. A hammer-type stapler as defined in claim 13 wherein said core member is mounted to slide longitudinally with respect to said housing member between the operating and loading positions thereof.

15. A hammer-type stapler as defined in claim 14 wherein said handle portion is hollow and said core member extends outwardly through and rearwardly beyond said hollow handle portion when in said loading position.

16. A hammer-type stapler as defined in claim 15 wherein said magazine assembly includes a releasable latch assembly constructed and arranged to releasably retain said core member in the operating position thereof.

17. A hammer-type stapler as defined in claim 16 wherein said latch assembly is constructed and arranged to retain said core member in the operating position thereof in a relationship enabling said core member to resiliently yieldingly move rearwardly in response to a staple jam occurrence during a staple drive stroke.

18. A hammer-type stapler as defined in claim 17 wherein said latch assembly includes a latch member mounted on the rearward end portion of said core member (1) for pivotal movement about a transverse axis between a core-retaining position and a core-releasing position and (2) for forward and rearward longitudinal movements with respect to said core member, and a spring acting between said housing member and said latch member resiliently biasing said latch member into said core-retaining position, the arrangement being such that when said latch member is in said core-retaining position said core member can be moved rearwardly against the bias of said spring.

19. A hammer-type stapler as defined in claim 1 wherein said drive track structure and said staple feed track structure are constructed and arranged so that the feed direction of guided movement of a staple stick along said feed track is at an angle greater than 90° with respect to the drive direction of the drive stroke of said driving element within said drive track so that a crown of a leading staple enters the drive track while a pair of legs of the leading staple are displaced angularly with respect to the direction of the drive stroke, and wherein said drive track structure is constructed and arranged to cause the leading staple to be moved into alignment with the drive track during the driving movement imparted to the crown thereof during said drive stroke enabling the hand grip portion to be positioned for manual gripping so that knuckles of a hand gripping the hand grip portion are spaced from a flat workpiece surface in which a staple has been driven generally perpendicularly therein.

20. A hammer-type stapler as defined in claim 19 wherein said staple drive track defining structure includes a staple-aligning assembly constructed and arranged to be yieldingly engaged beneath a forward crown portion of a leading staple disposed in said drive track slightly after said leading staple has been stripped from the staple stick during the drive stroke thereof to cause a pair of legs of the staple to move into alignment with a crown of the staple within said drive track.

21. A hammer-type stapler as defined in claim 20 wherein said staple-aligning assembly includes a ball mounted for fore and aft movement in said drive track structure in a position slightly below a crown of a leading staple moved into said drive track by said magazine loading and feeding mechanism, and a spring constructed and arranged to bias said ball so that a rearward portion thereof enters said drive track to be engaged and moved forwardly against the bias of said spring as the crown of the staple is moved thereby during the drive stroke thereof.

22. A hammer-type stapler as defined in claim wherein said staple drive track defining structure includes a staple-camming structure disposed rearwardly of said drive track constructed and arranged to engage the free ends of a pair of legs of a staple being driven in misalignment with said drive track and to cam the free ends of the legs of the staple into alignment with said drive track before moving outwardly thereof into the workpiece during the drive stroke thereof.

* * * * *